United States Patent
Isab et al.

(10) Patent No.: US 10,160,773 B2
(45) Date of Patent: *Dec. 25, 2018

(54) METHOD FOR INDUCING CYTOTOXICITY IN CANCER CELLS

(71) Applicant: King Fahd University of Petroleum and Minerals, Dhahran (SA)

(72) Inventors: Anvarhusein A. Isab, Dhahran (SA); Muhammad Altaf, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,723

(22) Filed: May 7, 2018

(65) Prior Publication Data

US 2018/0251477 A1 Sep. 6, 2018

Related U.S. Application Data

(63) Continuation of application No. 15/788,175, filed on Oct. 19, 2017, now Pat. No. 9,994,592.

(60) Provisional application No. 62/411,917, filed on Oct. 24, 2016.

(51) Int. Cl.
| | |
|---|---|
| *A61K 9/00* | (2006.01) |
| *C07F 1/00* | (2006.01) |
| *A61K 45/06* | (2006.01) |
| *A61K 31/28* | (2006.01) |
| *A61K 47/50* | (2017.01) |
| *A61P 35/00* | (2006.01) |

(52) U.S. Cl.
CPC ............ *C07F 1/005* (2013.01); *A61K 9/0053* (2013.01); *A61K 31/28* (2013.01); *A61K 45/06* (2013.01); *A61K 47/50* (2017.08); *A61P 35/00* (2018.01)

(58) Field of Classification Search
CPC ....................................................... C02F 1/4606
USPC ........................................................... 514/495
See application file for complete search history.

(56) References Cited

U.S. PATENT DOCUMENTS

| | | |
|---|---|---|
| 9,481,693 B1 | 11/2016 | Al-Jaroudi et al. |
| 9,487,542 B1 | 11/2016 | Al-Jaroudi et al. |
| 2017/0158713 A1 | 6/2017 | Isab et al. |

FOREIGN PATENT DOCUMENTS

| | | |
|---|---|---|
| CN | 102167704 | 5/2014 |
| EP | 1 545 512 | 3/2013 |

OTHER PUBLICATIONS

Di Hu et al., "Anticancer Gold(III) Porphyrins Target Mitochondrial Chaperone Hsp60," Dec. 9, 2015, vol. 128, No. 4, pp. 1409-1413.
Muhammad Altaf et al., "Synthesis, Structural Characterization, Electrochemical Behavior and Anticancer Activity of Gold(III) Complexes of Meso-1,2-di(1-Naphthyl)-1,2-Diaminoethane and Tetraphenylporophyrin," Royal Society of Chemistry, Aug. 1, 2016, vol. 40, No. 10, pp. 822-8295.
Taotao Zou et al., "Chemical Biology of Anticancer Gold(III) and Gold(I) Complexes," Chemical Society Reviews, vol. 8, No. 11, pp. 11824-11835.

*Primary Examiner* — Raymond J Henley, III
(74) *Attorney, Agent, or Firm* — Oblon, McClelland, Maier & Neustadt, L.L.P.

(57) ABSTRACT

A method for treating a proliferative disease, disorder, or condition comprising administering a gold(III) complex such as [Au(npen)Cl$_2$]Cl.2H$_2$O (1) or [Au(npen)$_2$]Cl$_3$ (2); the complexes, and methods for making them.

3 Claims, 6 Drawing Sheets

A549

MCF7

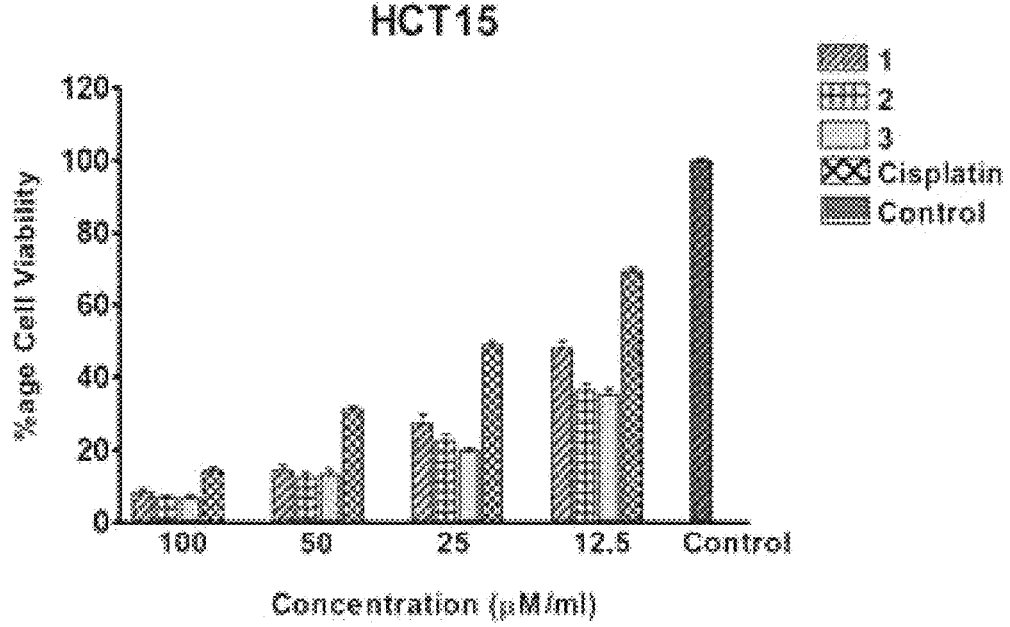

Core (1)

Core (2)

METHOD FOR INDUCING CYTOTOXICITY IN CANCER CELLS

CROSS-REFERENCE TO RELATED APPLICATIONS

The present application is a Continuation of Ser. No. 15/788,175, now allowed, having a filing date of Oct. 19, 2017, which claims priority to U.S. Provisional Application No. 62/411,917, having a filing date of Oct. 24, 2016, incorporated herein by reference in its entirety.

BACKGROUND

Field of the Invention

The present disclosure relates to gold(III) complexes of meso-1,2-di(1-naphthyl)-1,2-diaminoethane and to a method for inhibiting growth of cancer cells using them.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Today gold(III) complexes constitute an important class of potential anticancer agents because of their strong cytotoxic effects against selected human cancer cell lines; see B. Bertrand and A. Casini, Dalton Trans., 2014, 43, 4209-4219; C. Nardon, G. Boscutti and D. Fregona, Anticancer Res., 2014, 34, 487-492; S. Medici, M. Peana, V. M. Nurchi, J. L. Lachowicz, G. Crisponi and M. A. Zoroddu, Coord. Chem. Rev., 2015, 284, 329-350; R. W.-Y. Sun and C.-M. Che, Coord. Chem. Rev., 2009, 253, 1682-1691; I. Ott, Coord. Chem. Rev., 2009, 253, 1670-1681; A. Casini, C. Hartinger, C. Gabbiani, E. Mini, P. J. Dyson, B. K. Keppler and L. Messori, J. Inorg. Biochem., 2008, 102, 564-575; C.-M. Che and R. W.-Y. Sun, Chem. Commun., 2011, 47, 9554-9560; T. Zou, C. T. Lum, C.-N. Lok, J.-J. Zhang and C.-M. Che, Chem. Soc. Rev., 2015, 44, 8786-8801; W. Liu and R. Gust, Chem. Soc. Rev., 2013, 42, 755-773; A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149.

However, their low stability under physiological conditions remains a critical parameter in the drug development of these species because of their high reduction potential and fast hydrolysis rate; see A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149; L. Messori, F. Abbate, G. Marcon, P. Orioli, M. Fontani, E. Mini, T. Mazzei, S. Carotti, T. O. Connell and P. Zanello, J. Med. Chem., 2000, 43, 3541-3548; M. A. Cinellu, L. Maiore, M. Manassero, A. Casini, M. Arca, H.-H. Fiebig, G. Kelter, E. Michelucci, G. Pieraccini, C. Gabbiani and L. Messori, ACS Med. Chem. Lett., 2010, 1, 336-339; A. Casini, M. A. Cinellu, G. Minghetti, C. Gabbiani, M. Coronnello, E. Mini and L. Messori, J. Med. Chem., 2006, 49, 5524-5531.

These problems can possibly be circumvented by forming gold(III) compounds with one or more multidentate nitrogen-donor ligands to enhance their stability. See Dalton Trans., 2014, 43, 4209-4219; C. Nardon, G. Boscutti and D. Fregona, Anticancer Res., 2014, 34, 487-492; S. Medici, M. Peana, V. M. Nurchi, J. L. Lachowicz, G. Crisponi, and M. A. Zoroddu, Coord. Chem. Rev. 2015, 284, 329-350; R. W.-Y. Sun and C.-M. Che, Coord. Chem. Rev., 2009, 253, 1682-16911; I. Ott, Coord. Chem. Rev., 2009, 253, 1670-1681; A. Casini, C. Hartinger, C. Gabbiani, E. Mini, P. J. Dyson, B. K. Keppler and L. Messori, J. Inorg. Biochem., 2008, 102, 564-575; W. Liu and R. Gust, Chem. Soc. Rev. 2013, 42, 755-773; L. Messori, F. Abbate, G. Marcon, P. Orioli, M. Fontani, E. Mini, T. Mazzei, S. Carotti, T. O. Connell and P. Zanello, J. Med. Chem., 2000, 43, 3541-3548; and S. Carotti, A. Guerri, T. Mazzei, L. Messori, E. Mini and P. Orioli, Inorg. Chim. Acta., 1998, 281, 90-94, each incorporated herein by reference in their entirety.

In this regard, during the past two decades, promising antitumor gold(III) complexes containing nitrogen-donor polyaromatic ligands, such as terpyridine and phenanthroline derivatives, have been prepared and tested for their antitumor activity; see A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149; L. Messori, F. Abbate, G. Marcon, P. Orioli, M. Fontani, E. Mini, T. Mazzei, S. Carotti, T. O. Connell and P. Zanello, J. Med. Chem., 2000, 43, 3541-3548; M. A. Cinellu, L. Maiore, M. Manassero, A. Casini, M. Arca, H.-H. Fiebig, G. Kelter, E. Michelucci, G. Pieraccini, C. Gabbiani and L. Messori, ACS Med. Chem. Lett., 2010, 1, 336-339; A. Casini, M. A. Cinellu, G. Minghetti, C. Gabbiani, M. Coronnello, E. Mini and L. Messori, J. Med. Chem., 2006, 49, 5524-5531; G. Marcon, S. Carotti, M. Coronello, L. Messori, E. Mini, P. Orioli, T. Mazzei, M. A. Cinellu and G. Minghetti, J. Med. Chem., 2002, 45, 1672-1677; S. Carotti, A. Guerri, T. Mazzei, L. Messori, E. Mini and P. Orioli, Inorg. Chim. Acta, 1998, 281, 90-94; T. Yang, C. Tu, J. Zhang, L. Lin, X. Zhang, Q. Liu, J. Ding, Q. Xu and Z. Guo, Dalton Trans., 2003, 3419-3424; C. Martin-Santos, E. Michelucci, T. Marzo, L. Messori, P. Szumlas, P. J. Bednarski, R. Mas-Balleste, C. Navarro-Ranninger, S. Cabrera and J. Alemá n, J. Inorg. Biochem., 2016, 153, 339-345; A. A. Isab, M. N. Shaikh, M. Monim-ul-Mehboob, B. A. Al-Maythalony, M. I. M. Wazeer and S. Altuwaijri, Spectrochim. Acta, Part A, 2011, 79, 1196-1201; S. S. Al-Jaroudi, M. Fettouhi, M. I. M. Wazeer, A. A. Isab and S. Altuwaijri, Polyhedron, 2013, 50, 434-442; 20 M. Monim-ul-Mehboob, M. Altaf, M. Fettouhi, A. A. Isab, M. I. M. Wazeer, M. N. Shaikh and S. Altuwaijri, Polyhedron, 2013, 61, 225-234; and S. S. Al-Jaroudi, M. Monim-ul-Mehboob, M. Altaf, M. Fettouhi, M. I. M. Wazeer, S. Altuwaijri and A. A. Isab, New J. Chem., 2014, 38, 3199-3211.

Messori et al. reported the solution chemistry and the cytotoxic properties of several mono- and di-nuclear complexes, which include [Au(en)$_2$]Cl$_3$, [Au(phen)Cl$_2$]Cl, [Au2(phen2Me)$_2$(m-O)$_2$](PF$_6$)$_2$, [Au(bipy)(OH)$_2$][PF$_6$], [Au$_2$(2,20-bipyridine)$_2$(m-O)$_2$][PF$_6$]$_2$, [Au-(dien)$_2$Cl]Cl$_2$, [Au(terpy)Cl]Cl$_2$ and [Au(cyclam)](ClO$_4$)$_2$Cl; see A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149; L. Messori, F. Abbate, G. Marcon, P. Orioli, M. Fontani, E. Mini, T. Mazzei, S. Carotti, T. O. Connell and P. Zanello, J. Med. Chem., 2000, 43, 3541-3548; M. A. Cinellu, L. Maiore, M. Manassero, A. Casini, M. Arca, H.-H. Fiebig, G. Kelter, E. Michelucci, G. Pieraccini, C. Gabbiani and L. Messori, ACS Med. Chem. Lett., 2010, 1, 336-339; A. Casini, M. A. Cinellu, G. Minghetti, C. Gabbiani, M. Coronnello, E. Mini and L. Messori, J. Med. Chem., 2006, 49, 5524-5531; G. Marcon, S. Carotti, M. Coronello, L. Messori, E. Mini, P. Orioli, T. Mazzei, M. A.

Cinellu and G. Minghetti, J. Med. Chem., 2002, 45, 1672-1677; and S. Carotti, A. Guerri, T. Mazzei, L. Messori, E. Mini and P. Orioli, Inorg. Chim. Acta, 1998, 281, 90-94.

The coordination of polyamine ligands caused a marked stabilization of gold in the +3 oxidation state as indicated by measurements of the reduction potentials. With the exception of the cylam species, [Au(cyclam)]($ClO_4$)$_2$Cl, all complexes displayed good cytotoxic effects against different cancer cells; see L. Messori, F. Abbate, G. Marcon, P. Orioli, M. Fontani, E. Mini, T. Mazzei, S. Carotti, T. O. Connell and P. Zanello, J. Med. Chem., 2000, 43, 3541-3548; and S. Carotti, A. Guerri, T. Mazzei, L. Messori, E. Mini and P. Orioli, Inorg. Chim. Acta, 1998, 281, 90-94.

Gold(III) complexes of quinoline and its derivatives were also found to demonstrate significant tumor inhibition due to the formation of stable chelates. Some of them were even more active than cisplatin; see T. Yang, C. Tu, J. Zhang, L. Lin, X. Zhang, Q. Liu, J. Ding, Q. Xu and Z. Guo, Dalton Trans., 2003, 3419-3424; and C. Martín-Santos, E. Michelucci, T. Marzo, L. Messori, P. Szumlas, P. J. Bednarski, R. Mas-Balleste, C. Navarro-Ranninger, S. Cabrera and J. Alemán, J. Inorg. Biochem., 2016, 153, 339-345.

Recently, the inventors have evaluated the antiproliferative properties of some gold(III)-diamine complexes, particularly of 1,2-diaminocyclohexane, and the results illustrate that they possess promising anticancer activities against a number of cells. See A. A. Isab, M. N. Shaikh, M. Monim-ul-Mehboob, B. A. Al-Maythalony, M. I. M. Wazeer and S. Altuwaijri, Spectrochim Acta (A)., 2011, 79, 1196-1201; S. Al-Jaroudi, M. Fettouhi, M. I. M. Wazeer, A. A. Isab and S. Altuwaijri, Polyhedron, 2013, 50, 434-442; M. Monim-ul-Mehboob, M. Altaf, M. Fettouhi, A. A. Isab, M. I. M. Wazeer, M. N. Shaikh and S. Altuwaijri, Polyhedron, 2013, 61, 225-234; S. S. Al-Jaroudi, M. Monim-ul-Mehboob, M. Altaf, M. Fettouhi, M. I. M. Wazeer, S. Altuwaijri and A. A. Isab, New J. Chem., 2014, 38, 3199-3211; S. S. Al-Jaroudi, M. Monim-ul-Mehboob, M. Altaf, A. A. Al-Saadi, M. I. M. Wazeer, S. Altuwaijri and A. A. Isab, Biometals, 2014, 27, 1115-1136; S. S. Al-Jaroudi, M. Altaf, A. Al-Saadi, A.-N. Kawde, S. Altuwaijri, S. Ahmad and A. A. Isab, Biometals, 2015, 28, 827-844; and K. H. Omer, A. A. Seliman, M. Altaf, N. Casagrande, D. Aldinucci, S. Altuwaijri and A. A. Isab, Polyhedron, 2015, 102, 773-781, each incorporated herein by reference in their entirety.

Similarly, the in vitro cytotoxic evaluation of gold(III) complexes with esters of cyclohexyl-functionalized ethylenediamine-N,N'-diacetate or -dipropanoate showed that their cytotoxic action was comparable to that of cisplatin; see N. Pantelic, B. B. Zmejkovski, J. Trifunovic-Macedoljan, A. Savic, D. Stankovic, A. Damjanović, Z. Juranic, G. N. Kaluderović and T. J. Sabo, J. Inorg. Biochem., 2013, 128, 146-153; and N. Pantelic, T. P. Stanojkovic, B. B. Zmejkovski, T. J. Sabo and G. N. Kaluderovic, Eur. J. Med. Chem., 2015, 90, 766-774.

Gold(III)-dithiocarbamates have also received considerable attention as potential anticancer agents because of their strong cell growth-inhibitory effects. See L. Cattaruzza, D. Fregona, M. Mongiat, L. Ronconi, A. Fassina, A. Colombatti and D. Aldinucci, Int. J. Cancer., 2011, 128, 206-215; C. Marzano, L. Ronconi, F. Chiara, M. C. Giron, I. Faustinelli, P. Cristofori, Andrea Trevisan and Dolores Fregona, Int. J. Cancer., 2011, 129, 487-496; and L. Ronconi, L. Giovagnini, C. Marzano, F. Bettio, R. Graziani, G. Pilloni and D. Fregona, Inorg. Chem., 2005, 44, 1867-1881, each incorporated herein by reference in their entirety.

Gold(III) porphyrins might be regarded as a novel class of cytotoxic agents for nasopharyngeal carcinoma (NPC) and hepatocellular carcinoma (HCC) cells. See Medici et al.; Y. F. To, R. W.-Y. Sun, Y. Chen, V. S.-F. Chan, W.-Y. Yu, P. K.-H. Tam, C.-M. Che and C.-L. S. Lin, Int. J. Cancer., 2009, 124, 1971-1979; C. T. Lum, Z. F. Yang, H. Y. Li, R. W.-Y. Sun, S. T. Fan, R. T. P. Poon, M. C. M. Lin, C.-M. Che and H. F. Kung, Int. J. Cancer., 2006, 118, 1527-1538; and C. T. Lum, A. S.-T. Wong, M. C. M. Lin, C.-M. Che and R. W.-Y. Sun, Chem. Commun., 2013, 49, 4364-4366, each incorporated herein by reference in their entirety.

They were found to be stable in DMSO, as well as under physiologically-relevant conditions; see S. Medici, M. Peana, V. M. Nurchi, J. L. Lachowicz, G. Crisponi and M. A. Zoroddu, Coord. Chem. Rev., 2015, 284, 329-350.

A gold(III)-porphyrin complex, [Au(TPP)]Cl (H2TPP=tetraphenylporphyrin), exhibited potent in vitro anticancer activities towards a panel of cancer cell lines, including cisplatin- and multi-drug resistant cell lines. See C.-M. Che, R. W.-Y. Sun, W.-Y. Yu, C.-B. Ko, N. Zhu and H. Sun, Chem. Commun., 2003, 1718-1719, incorporated herein by reference in its entirety. Its toxicity to the cancer cells was B10 fold higher than to the normal cells, and thus it opened a safe therapeutic window for anti-NPC treatment; S. Medici, M. Peana, V. M. Nurchi, J. L. Lachowicz, G. Crisponi, and M. A. Zoroddu, Coord. Chem. Rev. 2015, 284, 329-350.

Moreover, in vivo and in vitro binding assays indicated that it interacted with the DNA in a non-covalent manner, which was different from cisplatin; see Y. Wang, Q.-Y. He, R. W.-Y. Sun, C.-M. Che and J.-F. Chiu, Eur. J. Pharmacol., 2007, 554, 113-122.

Based on the structural and electronic similarity of gold (III) complexes to cisplatin and related platinum antitumor drugs, it was thought that their activity was due to binding with DNA. But several studies indicate that DNA is not the main biological target of the gold(III) complexes since most of them are found to have weak binding affinity to DNA; see I. Ott, Coord. Chem. Rev., 2009, 253, 1670-1681; T. Zou, C. T. Lum, C.-N. Lok, J.-J. Zhang and C.-M. Che, Chem. Soc. Rev., 2015, 44, 8786-8801; A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149; A. Casini, M. A. Cinellu, G. Minghetti, C. Gabbiani, M. Coronnello, E. Mini and L. Messori, J. Med. Chem., 2006, 49, 5524-5531; Y. Wang, Q.-Y. He, R. W.-Y. Sun, C.-M. Che and J.-F. Chiu, Eur. J. Pharmacol., 2007, 554, 113-122; and L. Messori, P. Orioli, C. Tempi and G. Marcon, Biochem. Biophys. Res. Commun., 2001, 281, 352-360.

Gold(III) complexes on the other hand have shown high reactivity towards different protein models and inhibition of a few crucial proteins seems to be the main mechanism of action for cytotoxic gold complexes; see I. Ott, Coord. Chem. Rev., 2009, 253, 1670-1681; A. Casini, G. Kelter, C. Gabbiani, M. A. Cinellu, G. Minghetti, D. Fregona, H. H. Fiebig and L. Messori, J. Biol. Inorg. Chem., 2009, 14, 1139-1149; Y. Wang, Q. Y. He, C. M. Che and J. F. Chiu, Proteomics, 2006, 6, 131-142; and B. D. Glisic, U. Rychlewska and M. I. Djuran, Dalton Trans., 2012, 41, 6887-6901.

Particularly, in some studies proteasomes have been identified as the major in vitro and in vivo target for gold(III) complexes; see V. Milacic, D. Chen, L. Ronconi, K. R. L. Piwowar, D. Fregona and Q. P. Dou, Cancer Res., 2006, 66, 10478-10486; and V. Milacic and Q. P. Dou, Coord. Chem. Rev., 2009, 253, 1649-1660.

Moreover, these compounds are able to activate mitochondrial death pathways, since they markedly inhibit the activity of mitochondrial selenoenzyme, thioredoxin reductase; see N. Pantelic, T. P. Stanojkovic, B. B. Zmejkovski, T. J. Sabo and G. N. Kaluderovic, Eur. J. Med. Chem., 2015, 90, 766-774; and D. Saggioro, M. P. Rigobello, L. Paloschi, A. Folda, S. A. Moggach, S. Parsons, L. Ronconi, D. Fregona and A. Bindoli, Chem. Biol., 2007, 14, 1128-1139.

The structural and functional properties, including potential antitumor properties of gold(III)-diamine complexes have been studied; see A. A. Isab, M. N. Shaikh, M. Monim-ul-Mehboob, B. A. Al-Maythalony, M. I. M. Wazeer and S. Altuwaijri, Spectrochim. Acta, Part A, 2011, 79, 1196-1201; S. S. Al-Jaroudi, M. Fettouhi, M. I. M. Wazeer, A. A. Isab and S. Altuwaijri, Polyhedron, 2013, 50, 434-442; M. Monim-ul-Mehboob, M. Altaf, M. Fettouhi, A. A. Isab, M. I. M. Wazeer, M. N. Shaikh and S. Altuwaijri, Polyhedron, 2013, 61, 225-234; S. S. Al-Jaroudi, M. Monim-ul-Mehboob, M. Altaf, M. Fettouhi, M. I. M. Wazeer, S. Altuwaijri and A. A. Isab, New J. Chem., 2014, 38, 3199-3211; S. S. Al-Jaroudi, M. Monim-ul-Mehboob, M. Altaf, A. A. Al-Saadi, M. I. M. Wazeer, S. Altuwaijri and A. A. Isab, BioMetals, 2014, 27, 1115-1136; S. S. Al-Jaroudi, M. Altaf, A. Al-Saadi, A.-N. Kawde, S. Altuwaijri, S. Ahmad and A. A. Isab, BioMetals, 2015, 28,827-844 and K. H. Omer, A. A. Seliman, M. Altaf, N. Casagrande, D. Aldinucci, S. Altuwaijri and A. A. Isab, Polyhedron, 2015, 102, 773-781.

Herein is disclosed the synthesis, structural characterization, electrochemical evaluation, and newly described antiproliferative properties of two new gold(III) complexes 1 and 2 of a diamine, meso-1,2-di(1-naphthyl)-1,2-diaminoethane (npen). The interactions of 1 and 2 with model proteins were also studied by cyclic voltammetry. The cytotoxic (antitumor) activity of these gold(III) complexes was also evaluated against several different types of cancer cells including the MCF7 (breast cancer), HCT15 (colon cancer) and A549 (lung carcinoma) cell lines.

BRIEF SUMMARY OF THE INVENTION

The following provides a summary of certain exemplary embodiments of the present invention. This summary is not an extensive overview and is not intended to identify key or critical aspects or elements of the present invention or to delineate its scope.

The invention is directed to gold(III) complexes and to methods of treating cancer using these complexes. These gold(III) complexes have a significantly higher cytotoxicity against a variety of different cancer cells than cisplatin. Two complexes are exemplified, complex 1 and complex 2. The invention includes these complexes as well as their structural variants, for example, complexes having counterions other than chloride.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

FIGS. 4A, 4B and 4C. The survival of the A549 (FIG. 2A), MCF7 (FIG. 4B) and HCT15 (FIG. 4C) cells as a function of concentration of the complexes.

DETAILED DESCRIPTION OF THE INVENTION

Figure 1:
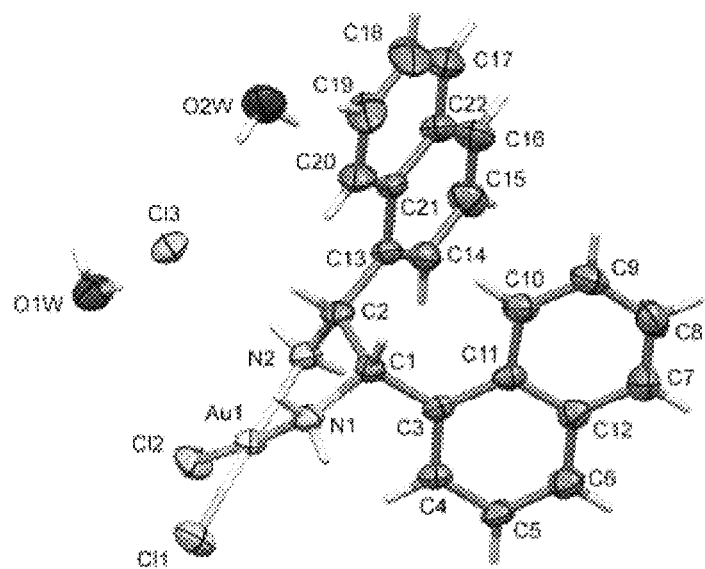
FIG. 1. The molecular structure of 1 along with atomic numbering scheme. The displacement ellipsoids are drawn at the 50% probability level.

The invention is directed to gold(III) complexes exemplified by (1) and (2) as well as their chemical variants as described herein. Gold(III) complexes, [Au(npen)Cl$_2$]Cl.2H$_2$O (1) and [Au(npen)$_2$]Cl$_3$ (2) have been synthesized and characterized using elemental analysis, IR and NMR spectroscopy, and one of them (1) by x-ray crystallography. The structure of 1 comprises [Au(npen)Cl$_2$] complex ion, chloride counter ion and two water molecules. The gold atom in complex ion adopts a distorted square planar geometry. The interactions of 1 and 2 with L-tyrosine, glutathione and lysozyme were studied electrochemically. The electrochemical measurements indicated that gold(III) remained stable and did not undergo reduction upon interaction with proteins. The in vitro cytotoxic properties of the complexes as well as of cisplatin were evaluated on three human cancer cell lines, A549 (lung cancer cells), MCF7 (breast cancer cells) and HCT15 (colon cancer cells) using MTT assay. The results indicated that gold(III) complexes according to the invention, such as preferred embodiments (1) and (2), were more potent than cisplatin in inhibiting growth of the selected cancer cells.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated. Thus, the two gold(III) complexes of the invention may be referred to as 1, complex 1, or compound 1; or 2, complex 2 or compound 2.

The term "active ingredient", as used herein, refers to an ingredient in the composition that is biologically active, for example, the gold(III) complex disclosed herein, a salt thereof, a prodrug thereof, or a solvate thereof. Other active ingredients include, but are not limited to, those that exert a substantial pharmacokinetic or pharmacodynamic actitity when in admixture with a Gold(III) complex, for example, other anti-cancer drugs, immunopotentiators, or agents.

Antitumor properties may be evaluated by methods known in the art, including these described by and incorporated by reference to Y. F. To, R. W.-Y. Sun, Y. Chen, V. S.-F. Chan, W.-Y. Yu, P. K.-H. Tam, C.-M. Che and C.-L. S. Lin, Int. J. Cancer, 2009, 124, 1971-1979; C. T. Lum, Z. F. Yang, H. Y. Li, R. W.-Y. Sun, S. T. Fan, R. T. P. Poon, M. C. M. Lin, C.-M. Che and H. F. Kung, Int. J. Cancer, 2006, 118, 1527-1538; C. T. Lum, A. S.-T. Wong, M. C. M. Lin, C.-M. Che and R. W.-Y. Sun, Chem. Commun., 2013, 49, 4364-4366; C.-M. Che, R. W.-Y. Sun, W.-Y. Yu, C.-B. Ko, N. Zhu and H. Sun, Chem. Commun., 2003, 1718-1719; Y. Wang, Q.-Y. He, R. W.-Y. Sun, C.-M. Che and J.-F. Chiu, Eur. J. Pharmacol., 2007, 554, 113-122.

Cytotoxic activity. In one embodiment, the $IC_{50}$ of the gold(III) complexes is in a range of 0.01-200 μM, 0.1-100 μM, 1-100 μM, 10-90 μM, 20-80 μM, 30-80 μM, 40-80 μM, 50-80 μM, or 50-75 μM. These ranges include all intermediate subranges and values.

As used herein, the term "$IC_{50}$" refers to a concentration of a gold(III) complex, the salt thereof, the prodrug thereof, or the solvate thereof, which causes the death of 50% of cancer or proliferating cells in 72 hours (3 days) such as the A549, MCF-7, or HTC15 cancer cell lines described herein. The $IC_{50}$ can be determined by standard cell viability assays, such as, without limitation, ATP test, calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. Preferably, a MTT assay and/or a Trypan Blue assay is used.

Biomarkers. Alternatively to use of $IC_{50}$ values, efficacy of treatment with a gold(III) complex of the invention may be determined by measuring or detecting a change in one or cancer biomarkers, for example, comparing quantity of biomarkers in a blood or tissue sample before and after a treatment.

A treatment may significantly decrease the concentration of a particular biomarker, for example, by 5, 10, 15, 20, 25, 30, 35, 40, 45, 50, 55, 60, 65, 70, 75, 80, 85, 90, or 100%, compared to a control or pre-treatment value. As used herein, the term "biomarker" refers to a characteristic that is objectively measured and evaluated as an indicator of normal biological processes, pathogenic processes or pharmacological responses to a therapeutic intervention. Biomarkers include ER/PR, HER-2/neu for breast cancer, EGFR, KRAS, UGT1A1 for colorectal cancer, EML4/ALK, EGFR, and KRAS for lung cancer as well as other biomarkers described and incorporated by reference to https://_en.wikipedia.org/wiki/Cancer_biomarkers (last accessed Aug. 11, 2017). Cancer biomarkers are useful in determining the aggressiveness of an identified cancer as well as its likelihood of responding to the treatment. Examples of such prognostic biomarkers include, without limitation, CA125, β2-microglobulin, and EBV DNA. A change or mutation in a biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art. The concentration of the biomarker may be measured with an assay, for example an antibody-based method (e.g., an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like. Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences. The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor. In some embodiments, the concentration of the biomarker is measured before and after the administration. When the concentration of the biomarker is maintained, the method may further comprise increasing the effective amount of at least one of the gold(III) complex of the invention, the salt thereof, the solvate thereof, the prodrug thereof, and the combination thereof by at least 5%, at least 10%, or at least 30%, up to 50%, up to 60%, or up to 80% of an initial effective amount that is in a range of 1-100 mg/kg based on the weight of the subject. The subject may be administered with the increased dosage for a longer period (e.g. 1 week more, 2 weeks more, or 2 months more) than the duration with the initial effective amount. In some embodiments, the mutation in the biomarker is detected before administrating the composition to identify subjects predisposed to the disease. For example, women with a BRCA1 germline mutation are at a higher risk of contracting ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

The term "counter-anion" refers to an anion, preferably a pharmaceutically acceptable anion, that is associated with a positively charged gold(III) complex. Non-limiting examples of pharmaceutically counter-anions include nitrate, halides such as fluoride, chloride, bromide, iodide; nitrate; sulfate; phosphate; amide; methanesulfonate; ethanesulfonate; p-toluenesulfonate, salicylate, malate, maleate, succinate, tartrate; citrate; acetate; perchlorate;

trifluoromethanesulfonate (triflate); acetylacetonate; hexafluorophosphate; and hexafluoroacetylacetonate.

Figure 7A:
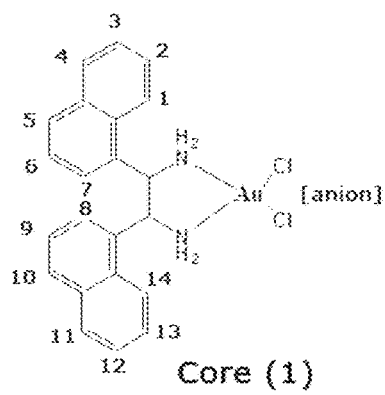
FIGS. 7A and 7B. Core structures 1 and 2.
Figure 7B:
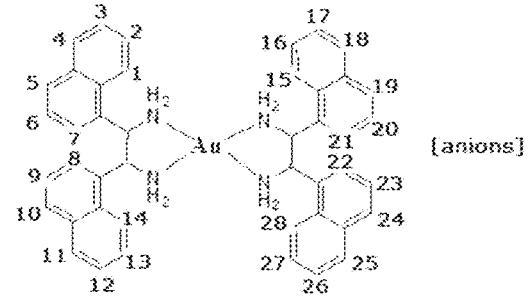
Figure 8A:
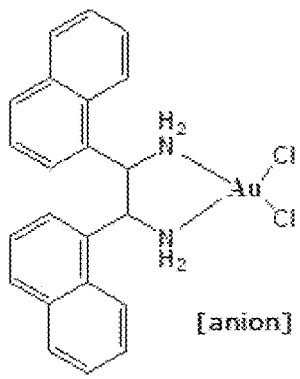
FIGS. 8A and 8B. Complexes (1) (FIG. 8A) and (2) (FIG. 8B). In some embodiments complex (1) will have a single Cl$^-$ anion associated with it and may be hydrated by two water molecules, and complex (2) will have three Cl$^-$ ions associated with it.
Figure 8B:
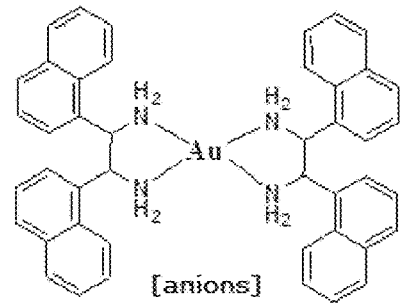

Variants. Some embodiments of the gold(III) complexes invention will constitute variants of chemical structures of complexes 1 and 2 shown by FIGS. 7A and 7B. For example, such variants may comprise different counterions as described above or have one or more other substituents on the naphthyl rings depicted by FIG. 7A or 7B.

"Other substituents" that may appear on the naphthyl rings of variants of 1 and 2 include, but are not limited those defined below.

The term "alkyl", as used herein, unless otherwise specified, refers to a straight or branched hydrocarbon fragment such as a $C_1$-$C_6$ group. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, 1-methylcyclopropyl and 2-methycyclopropyl groups, are included in the definition of cycloalkyl as used in the present disclosure. The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl. The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), IH-indolyl, isoquinolyl (or its N-oxide), or quinolyl (or its N-oxide), for example. As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined hereinafter); halogen (e.g. chlorine, bromine, fluorine or iodine); alkoxy (i.e. straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl); hydrocarbyl; arylalkyl; hydroxy; alkoxy; oxo; alkanoyl; alkanoyloxy; amino; alkylamino; arylamino; arylalkylamino; disubstituted amines (e.g., in which the two amino substituents are selected from the exemplary group including, but not limited to, alkyl, aryl, or arylalkyl); alkanoylamino; thiol; alkylthio; arylthio; arylalkylthio; alkylthiono; arylthiono; aryalkylthiono; alkylsulfonyl; arylsulfonyl; arylalkylsulfonyl; sulfonamido (e.g., —$SO_2NH_2$); substituted sulfonamide; nitro; cyano; carboxy; carbamyl (e.g., —$CONH_2$, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety). The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl. The term "alkylthio" as used in this disclosure refers to a divalent sulfur with alkyl occupying one of the valencies and includes the groups methylthio, ethylthio, propylthio, butylthio, pentylthio, hexylthio, and octylthio. The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl. Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring. The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl. The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolylcarbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl. "Vinyl" refers to an unsaturated substituent having at least one unsaturated double bond and having the formula $CH_2=CH-$. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl. The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

Compositions. In most embodiments, the gold(III) complexes of the invention, the salt thereof, the solvate thereof, a prodrug thereof, or a combination thereof is formulated in a pharmaceutically acceptable composition. As used herein, a "composition" refers to a mixture of the active ingredient with other chemical components, such as pharmaceutically acceptable carriers and excipients. One purpose of a composition is to facilitate administration of the gold(III) complex of the invention, the salt thereof, the solvate thereof, the prodrug thereof, or a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage. The phrase "pharmaceutically acceptable" as used herein refers to compounds, counterions, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo, ex vivo, or in vitro.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g., about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

Other active ingredients. In some embodiments, other active ingredients in addition to the gold(III)complex may be incorporated into a composition or separately administered in conjunction with a gold(III) complex. In one embodiment, the composition is used for treating cancer and further comprises a second active ingredient, such as a chemotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder. Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-50 wt % of the second active ingredient, preferably 10-40 wt %, more preferably 10-20 wt %, relative to the weight of the first active ingredient.

Subjects. The terms "patient", "subject", and "individual" are used interchangeably. As used herein, they refer to individuals suffering from a disease, at risk of further progression of a disease, or at risk of acquiring or developing the disease. None of the terms require that the individual be under the care and/or supervision of a medical professional.

These terms generally refer to humans, but also apply to mammals, avians and other animals especially domesticated or ecologically or commercially valuable animals. Mammals include non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In a preferred embodiment, the subject is a human.

A "subject in need of treatment" includes a subject already with the disease, a subject which does not yet experience or exhibit symptoms of the disease, and a subject predisposed to the disease. In preferred embodiments, the subject is a person who is predisposed to cancer, e.g. a person with a family history of cancer. In another embodiment, the subject refers to a cancer patient who has been previously administered/treated with cisplatin and have cisplatin resistance (for example in the form of high ERCC1 mRNA levels, overexpression of HER-2/neu, activation of the PI3-K/Akt pathway, loss of p53 function, and/or overexpression of antiapoptotic bcl-2).

Cancers/Proliferative Disorders. Cancers such as, but not limited to sarcomas, carcinomas, melanomas, myelomas, gliomas and lymphoma (including Hodkin lymphoma), can be treated or prevented with the gold(III) complexes provided herein.

In some embodiments, methods incorporating the use a gold(III) complex of the present disclosure to treat or prevent cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system. In some embodiments, these methods are effective in the treatment or prevention of cervical, colon and lung cancers. Cancers or tumor resistant to other anticancer drugs, such as cisplatin-resistant cancers, may be treated. In treating certain cancers, the best approach is often a combination of surgery, radiotherapy, and/or chemotherapy. Therefore, in at least one embodiment, the composition is employed in conjunction with conventional radiotherapy and/or chemotherapy. In another embodiment, the composition is employed with surgery. The radiotherapy and/or surgery may be before or after the composition is administered.

Other non-cancerous proliferative diseases, disorders or conditions may also be treated, such as atherosclerosis, rheumatoid arthritis, psoriasis, idiopathic pulmonary fibrosis, scleroderma, cirrhosis of the liver, or benign proliferative conditions such as verruca (warts), dermatitis, or other disorders characterized by epidermal cell proliferation.

Therapy. As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

Administration. The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection including intravenous, subcutaneous, intraperitoneal, intramuscular, intravascular, or infusion, topical and rectal administration. Those of ordinary skill in the art are familiar with administration techniques that can be employed with the compounds and methods described herein. In preferred embodiments, the active ingredient and/or the composition described herein are administered orally.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the gold(III) complex of the invention, the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, or tolerance and resistance of the body to the administered drug, and then determined and adjusted accordingly. In at least one embodiment, the at least one of the gold(III) complex of the invention, the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg.

In some embodiments, a treatment will involve administering a composition comprising at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the gold(III) complex of the invention. The composition may comprise 0.01-50 µM, 0.01-30 µM, preferably 0.01-10 µM of the gold(III) complex of the invention relative to the total composition. In some embodiments, the composition comprises up to 0.1 wt %, 1 wt %, 5 wt %, or 10 wt % of the pharmaceutically acceptable salt of the gold(III) complex of the invention. In some embodiments, the composition comprises up to 0.1 wt %, 1 wt %, 5 wt %, or 10 wt % of the pharmaceutically acceptable solvate thereof of either the gold(III) complex of the invention. These ranges include all intermediate subranges and values.

A treatment method may comprise administering a composition containing the gold(III) complex of the invention as a single dose or multiple individual divided doses. In some embodiments, the composition is administered at various dosages (e.g., a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

EMBODIMENTS

The following examples illustrate various aspects of the present invention. They are not to be construed to limit the claims in any manner whatsoever.

1. A method for inducing cytotoxicity in a subject in need thereof comprising administering Au(npen)Cl$_2$] Cl•2H$_2$O ("complex 1") or [Au(npen)$_2$]Cl$_3$ ("complex 2") to the subject or a variant complex in which the chloride counterions of complex 1 or 2 are replaced with other counterions and/or where the naphthyl rings of complex 1 or complex 2 are substituted with at least one non-hydrogen substituent.

2. The method of embodiment 1 that comprises administering Au(npen)Cl$_2$]Cl•2H$_2$O ("complex 1").
3. The method of embodiment 1 that comprises administering [Au(npen)$_2$]Cl$_3$ ("complex 2").
4. The method of embodiment 1, wherein the subject has a proliferative disease, disorder or condition.
5. The method of embodiment 1, wherein the subject has cancer.
6. The method of embodiment 1, wherein the subject has breast cancer.
7. The method of embodiment 1, wherein the subject has lung cancer.
8. The method of embodiment 1, wherein the subject has colon cancer.
9. The method of embodiment 1, wherein the complex is administered orally.
10. The method of embodiment 1, wherein the complex is administered parenterally.
11. The method of embodiment 1, wherein the complex is administered into a tumor or into a site infiltrated by cancer cells.
12. The method of embodiment 1, wherein the complex is administered along with a radiation treatment.
13. The method of embodiment 1, wherein the complex is administered before, during or after a surgical treatment.
14. The method of embodiment 1, wherein the complex is administered before, simultaneously, or after treatment with an anticancer drug, chemotherapeutic agent, or immunopotentiator.
15. A gold(III) complex selected from the group consisting of Au(npen)Cl$_2$]Cl•2H$_2$O ("complex 1") and [Au(npen)$_2$]Cl$_3$ ("complex 2"); or a variant complex in which the chloride counterions of complex 1 or 2 are replaced with other counterions, and/or where the naphthyl rings of complex 1 or complex 2 are substituted with at least one non-hydrogen substituents.
16. The gold(III) complex of embodiment 15 that comprises Au(npen)Cl$_2$]Cl•2H$_2$O ("complex 1").
17. The gold(III) complex of embodiment 15 that comprises [Au(npen)$_2$]Cl$_3$ ("complex 2").
18. A pharmaceutical composition comprising at least one gold(III) complex of embodiment 15 in combination with at least one pharmaceutically acceptable carrier or excipient.
19. The pharmaceutical composition of embodiment 18 that further comprises an anticancer drug or chemotherapeutic agent.
20. The pharmaceutical composition of embodiment 18 that further comprises an immunopotentiator.

Example 1

Synthesis of Gold(III) Complexes

Sodium tetrachloridoaurate(III) dihydrate (NaAuCl$_4$.2H$_2$O) and meso-1,2-di(1-naphthyl)-1,2-diaminoethane (npen) were purchased from Sigma-Aldrich Chemical Co. L-tyrosine, lysozyme, 1-glutathione, ethanol, sodium dihydrogen phosphate, and disodium hydrogen phosphate was purchased from Sigma-Aldrich (USA). The double distilled water was used for electrochemical measurements and obtained from Lab based Water Still Aquatron A 4000 D unit. (3-(4,5-Dimethylthiazol-2-yl)-2,5-diphenyltetrazolium bromide, a yellow tetrazole) was purchased from Sigma Chemical Co, St. Louis, Mo., USA.

The complexes 1, [Au(npen)Cl$_2$]Cl.2H$_2$O and 2, [Au(npen)$_2$]Cl$_3$ were prepared by mixing 200 mg (0.5 mmol) NaAuCl$_4$.2H$_2$O and 157 mg (0.5 mmol) or 315 mg (1 mmol) meso-1,2-di(1-naphthyl)-1,2-diaminoethane (npen) for complexes 1 and 2 respectively, in 20 mL water and stirring the mixture continuously for 1 hour. The resulting orange (for 1) or yellow (for 2) precipitates were collected by filtration. The products were dried in air at room temperature. Yield: 86% (280.88 mg) for complex 1 and 79% (366.87 mg) for complex 2. Suitable crystals of complex 1 were obtained as small golden-yellow rods by slow evaporation of its methanol/water solution. The elemental analysis of the complexes are given in Table 1.

TABLE 1

Elemental Analysis and melting Points of Gold(III) complexes

| Compound | Found (Calculated) % | | |
|---|---|---|---|
| | C | H | N |
| 1 | 39.98 (40.54) | 3.81 (3.71) | 4.25 (4.30) |
| 2 | 57.15 (56.94) | 4.28 (4.34) | 5.97 (6.04) |

IR and NMR Measurements

IR spectra of the ligands and their gold(III) complexes were recorded on a Perkin-Elmer FT-IR 180 spectrophotometer using KBr pellets over the range 4000-400 cm$^{-1}$. All NMR measurements were carried out on a Jeol JNM-LA 500 NMR spectrophotometer at 297K. The $^1$H NMR spectra were recorded at a frequency of 500.00 MHz. The $^{13}$C NMR spectra were obtained at a frequency of 125.65 MHz with $^1$H broadband decoupling and referenced relative to TMS. The spectral conditions were: 32 k data points, 0.967 s acquisition time, 1.00 s pulse delay and 45 degrees pulse angle.

Spectroscopic Data

IR (KBr pellet, cm$^{-1}$): npen, ν=3384, 3317, 3051, 2900, 1594, 1507, 1386, 1260, 1139, 1075, 994; 1, ν=3446, 2916, 2852, 1647, 1513, 1403, 1268, 774; 2, ν=3414, 3040, 2924, 2857, 1514, 776; TPP, ν=3449, 3300, 3053, 1596, 1440, 1347, 1069, 1002, 967, 793, 726, 695.

$^1$H NMR (500 MHz, DMSO, 24° C., TMS, ppm): npen, δ=1.84, 5.08, 7.26, 7.33, 7.40, 7.50, 7.71, 7.84, 7.86; 1, δ=1.21, 5.89, 7.24, 7.34, 7.40, 7.54, 7.95, 7.97, 10.40; 2, δ=5.45, 7.1-9.1 (multiplet); TPP, δ=7.81, 8.11, 8.20, 8.84.

$^{13}$C NMR (125.65 MHz, DMSO, TMS, ppm): npen, δ=50.60, 123.27, 124.52, 125.18, 126.85, 128.45, 131.73, 133.06, 139.59, 177.89; 1, δ=51.86, 125.04, 125.87, 126.11, 126.63, 127.95, 128.77, 129.73, 130.50, 178.53; 2, 52.28, 122.25, 124.82, 125.55, 126.04, 128.50, 130.96, 132.43, 132.71, 178.65.

The IR spectrum of npen showed the N—H, C—H, C—N absorption stretching bands at 3384 & 3317, 3053 & 2900 and 1002 cm$^{-1}$ respectively. The N—H bending vibration was observed at 1594 cm$^{-1}$. These bands also appeared in the spectra of 1 and 2 suggesting the formation of these complexes. The IR spectrum of TPP is characterized by the N—H, C—H, C=N and C=C stretching vibrations, which were observed at 3300, 3053, 1596 and 1468 and 1440 cm$^{-1}$ respectively. Broad peaks around 3440 cm$^{-1}$ represent the O—H groups. The aromatic C—H bending vibrations were observed around 700 cm$^{-1}$.

The NMR data of the ligands and complexes is listed in section 2.4. In $^1$H NMR spectrum of npen, the $CH_2$ and N—H resonances were observed at 1.84 and 5.08 ppm respectively. For aromatic protons, the expected seven signals were observed between 7 and 8 ppm. In the spectrum of 1 these resonances were also clear but in case of 2 a bunch of peaks was observed in the region of 7.5-9.1 ppm. The $^1$H NMR spectra of TPP and its complex showed four signals associated to aromatic protons. In $^{13}$C NMR spectra of npen and its complexes 1 and 2 the $CH_2$ resonance of npen was observed around 51 ppm. Nine signals were observed for the aromatic carbon atoms of npen; the one at 128 ppm being more intense represents two carbon atoms. The C-1 atom of naphthyl attached to diamino ethane appeared at the most downfield position. Upon coordination, the resonances were shifted slightly downfield. The downfield shift is attributed to the shift of electron density from the ligand towards the metal.

X-Ray Structural Determination

The intensity data of 1 were collected at 203 K (−70° C.) on a Stoe Mark II-Image Plate Diffraction System equipped with a two-circle goniometer and using MoKα graphite monochromated radiation (λ=0.71073 Å). See Stoe & Cie. (2009). X-Area & X-RED32. Stoe & Cie GmbH, Darmstadt, Germany, incorporated herein by reference in its entirety. The structure was solved by direct methods with SHELX-97. See G. M. Sheldrick, *Acta Crystallogr. A.*, 2008, 64, 112, incorporated herein by reference in its entirety. The refinement and all further calculations were carried with SHELX-2014. See G. M. Sheldrick, Acta Cryst., 2015, C71, 3-8, incorporated herein by reference in its entirety. All the H atoms could be located in difference Fourier maps.

In the final cycles of refinement, the water H atoms were refined with distance restraints (O—H=0.84(2) A and H . . . H=1.35(2) Å) with $U_{iso}$(H)=1.5 $U_{eq}$(O). The $NH_2$ and C-bound H atoms were included in calculated positions and treated as riding atoms: N—H=0.90 Å and C—H=0.94-0.99 Å with $U_{iso}$(H)=1.2 $U_{eq}$(C). The non-H atoms were refined anisotropically, using weighted full-matrix least squares on F2. A semi-empirical (multi-scan) absorption correction was applied using the MULABS routine in PLATON. See A. L. Spek, *Acta Cryst.*, 2009, D65, 148-155, incorporated herein by reference in its entirety. The figures were drawn using the program, Mercury. See C. F. Macrae, I. J. Bruno, J. A. Chisholm, P. R. Edgington, P. M. Cabe, E. Pidcock, L. Rodriguez-Monge, R. Taylor, J. Streek and P. A. Wood, *J. Appl. Cryst.*, 2008, 41, 466-470, incorporated herein by reference in its entirety. A summary of crystal data and refinement details for compound 1 is given in Table 2.

TABLE 2

| Crystal data and structure refinement details of compound 1. | |
|---|---|
| CCDC deposit no. | 1447950 |
| Chemical formula | $C_{22}H_{20}AuCl_2N_2^+ \cdot Cl^- \cdot 2(H_2O)$ |
| Molecular weight | 651.75 |
| Crystal system, space group | Triclinic, P-1 |
| Temperature (K) | 203 |
| a, b, c (Å) | 9.1800 (6), 9.4741 (6), 14.4358 (10) |
| A, β, γ (°) | 90.556 (6), 107.977 (5), 97.243 (5) |
| V (Å$^3$) | 1183.12 (14) |
| Z | 2 |
| μ (mm−1) | 6.58 |
| Crystal size (mm) | 0.20 × 0.10 × 0.10 |
| $T_{min}$, $T_{max}$ | 0.773, 1.000 |
| No. of measured, independent and observed [I > 2σ(I)] reflections | 13452, 4761, 4057 |
| $R_{int}$ | 0.070 |
| (sin θ/λ)$_{max}$ (Å$^{-1}$) | 0.621 |
| R[F$^2$ > 2σ(F$^2$)], wR(F$^2$), S | 0.039, 0.091, 0.99 |
| No. of restraints | — |
| No. of parameters | 283 |
| Largest diff. Peak and hole (e Å$^{-3}$) $\Delta\rho_{max}$, $\Delta\rho_{min}$ (e Å$^{-3}$) | 1.59, −2.55 |

The molecular crystal structure of complex 1 is shown in FIG. 1.

The selected bond distances and angles are given in Table 3.

Figure 2:
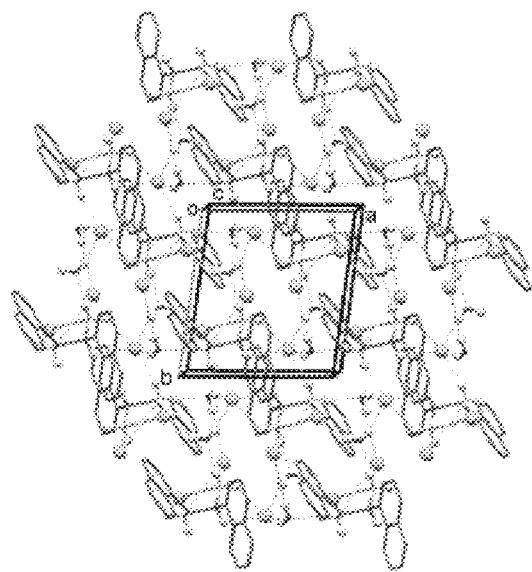
FIG. 2. The crystal packing of the complex 1, viewed along the c axis. Illustrating the formation of the hydrogen bonded two-dimensional network parallel to the ab plane.
Figure 3:
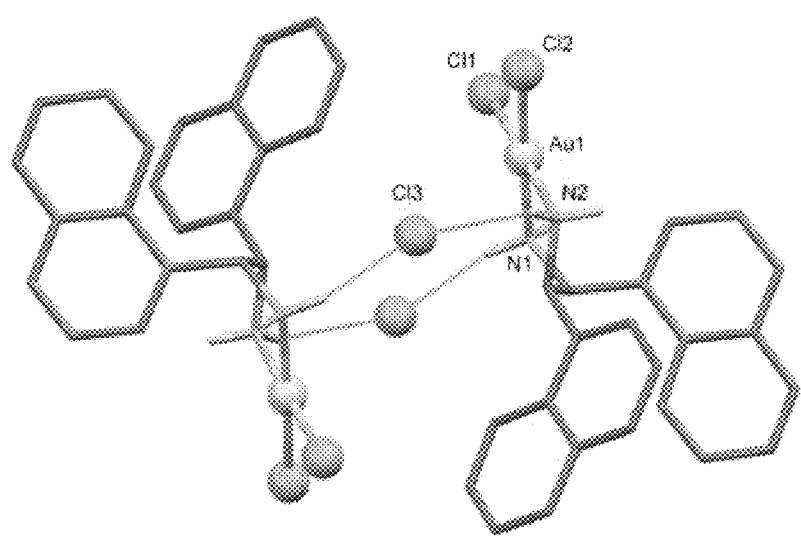
FIG. 3. A view of the formation of the dimer of 1 formed by N—H . . . Cl hydrogen bonds involving the Cl$^-$ anion.

The complex 1 is mononuclear and consists of a complex cation, [Au(npen)Cl$_2$]$^+$, a chloride counter ion and two water molecules of crystallization. The central gold(III) ion in 1 is coordinated by two nitrogen atoms of the meso-1,2-di-1-Naphthyl-ethylenediamine (npen) ligand and two chloride ions. It adopts a somewhat distorted square planar geometry as indicated by the bond angles around gold center (Table 3). The N—Au—N cis angle of 83.8(2) is less than 90° owing to the strain of the diamine ligand after coordination. The trans angles (175.11(2)°) are close to linear geometry. These values are in agreement with the values of other gold(III)-diamine complexes. See S. Zhu, W. Gorski, D. R. Powell and J. A. Walmsley, *Inorg. Chem.*, 2006, 45, 2688-2694; and D. M. Motley, J. A. Walmsle, J. Zukerman-Schpector and E. R. T. Tiekink, *J. Chem. Crystallogr.*, 2009, 39, 364-367, each incorporated herein by reference in their entirety. The Au—N bond distances in 1 are almost equal (2.034(5) and 2.029(6) Å), and resemble to those in [Au{cis/trans-(±)-1,2-DACH}Cl$_2$]Cl. See S. S. Al-Jaroudi, M. Fettouhi, M. I. M. Wazeer, A. A. Isab and S. Altuwaijri, *Polyhedron*, 2013, 50, 434-442, incorporated herein by reference in its entirety. However, they are somewhat different from the Au—N distances in [Au(en)Cl$_2$]Cl.2H$_2$O, [Au(en)Cl$_2$]NO$_3$ and [Au{1R,2R-(−)-1,2-DACH}Cl$_2$]Cl.0.5H$_2$O. See K. H. Omer, A. A. Seliman, M. Altaf, N. Casagrande, D. Aldinucci, S. Altuwaijri and A. A. Isab, *Polyhedron*, 2015, 102, 773-781; S. Zhu, W. Gorski, D. R. Powell and J. A. Walmsley, *Inorg. Chem.*, 2006, 45, 2688-2694; and D. M. Motley, J. A. Walmsle, J. Zukerman-Schpector and E. R. T. Tiekink, *J. Chem. Crystallogr.*, 2009, 39, 364-367, each incorporated herein by reference in their entirety. The Au—Cl bond distances of 2.272(2) and 2.274(2) Å are very close to the reported values of the related structures. See S. S. Al-Jaroudi, M. Fettouhi, M. I. M. Wazeer, A. A. Isab and S. Altuwaijri, *Polyhedron*, 2013, 50, 434-442; M. Monim-ul-Mehboob, M. Altaf, M. Fettouhi, A. A. Isab, M. I. M. Wazeer, M. N. Shaikh and S. Altuwaijri, *Polyhedron*, 2013, 61, 225-234; K. H. Omer, A. A. Seliman, M. Altaf, N. Casagrande, D. Aldinucci, S. Altuwaijri and A. A. Isab, *Polyhedron*, 2015, 102, 773-781; S. Zhu, W. Gorski, D. R. Powell and J. A. Walmsley, *Inorg. Chem.*, 2006, 45, 2688-2694; and D. M. Motley, J. A. Walmsle, J. Zukerman- Schpector and E. R. T. Tiekink, *J. Chem. Crystallogr.,* 2009, 39, 364-367, each incorporated herein by reference in their entirety. The complex cation and chloride ions are associated to each other through electrostatic and H-bonding interactions. All the chloride ions, both amine groups and water molecules are engaged in hydrogen bonding with each other. The complex molecules pack head to head to generate molecular chains along the a and c axes (FIG. 2). The N—H . . . Cl hydrogen bonding interactions involving the Cl⁻ anion result in the formation of a dimer as shown in FIG. 3.

Protein Interaction Studies by Electrochemical Measurements

The voltammetric measurements were performed by using three electrode based Auto Lab electrochemical workstation (Netherland). The working electrode was glassy carbon electrode (GCE), while Ag/AgCl and platinum were used as reference counter electrodes respectively. The weights of the chemicals were measured by using GR-2000 electrical balance. The pH of the buffer was controlled by Accumet® XL50 pH meter. For electrochemical analysis, the the compounds 1 and 2 were dissolved in the ethanol as their solubility was very poor in aqueous medium. Prior to each analysis, the GCE was polished as a mirror like surface with alumina slurry on the synthetic clothe. The cyclic voltammograms for various analyses were recorded from 0.0 V to +1.3 V with a scan rate of 0.1 V/s. Electrochemical behavior may be studied using the methods described by Al-Jaroudi et al. and Seliman et al. (incorporated by reference) and well known model proteins. See S. S. Al-Jaroudi, M. Altaf, A. Al-Saadi, A.-N. Kawde, S. Altuwaijri, S. Ahmad and A. A. Isab, *Biometals,* 2015, 28, 827-844; and A. Seliman, M. Altaf, A. Kawde, M. Wazeer and A. Isab, *J. Coord. Chem.,* 2014, 67, 3431-3443, each incorporated herein by reference in their entirety.

Figure 5A:
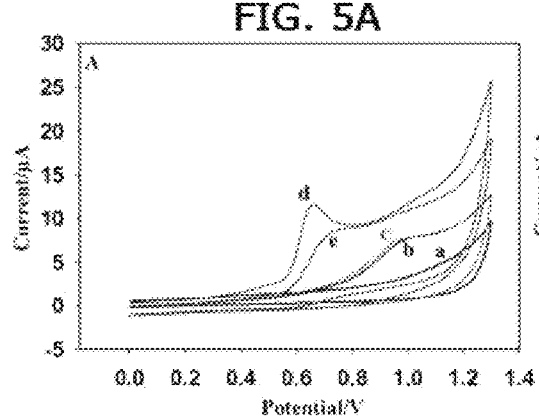
FIGS. 5A and 5B. Cyclic voltammograms in 0.1 M phosphate buffer solution (pH 7.0) of 1 (FIG. 5A) and 2 (FIG. 5B): (a) blank, (b) 0.1 mM complex, (c) addition of 192 µL of L-tyrosine solution solvent blank, and 320 µM L-tyrosine in absence (d), and presence (e) of 320 µM L-0.1 mM complex at GCE. The cyclic voltammograms were recorded at 0.1 V/s scan rate, and 120 s adsorption time.
Figure 5B:
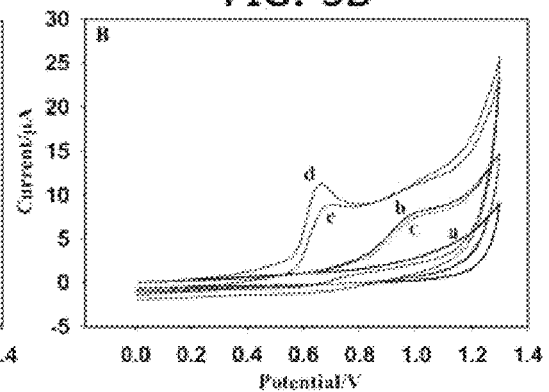
Figure 6A:
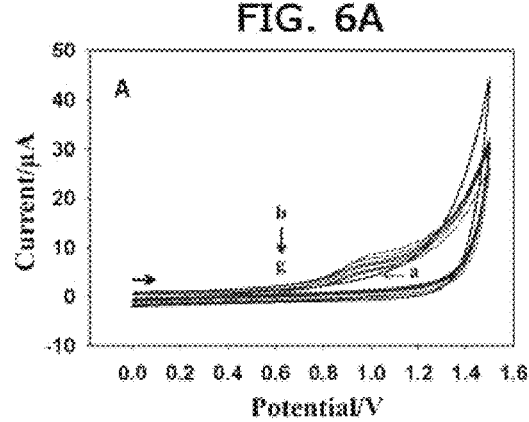
FIGS. 6A, 6B, 6C and 6D Cyclic voltammograms of 1 (FIG. 6A) and 2 (FIG. 6B) and corresponding control experiment A' (FIG. 6C) and B' (FIG. 6D) in 0.1 M phosphate buffer solution (pH 7.0). (a, a') blank, 0.1 mM MR57 (A) or MR58 (B) in presence of glutathione at different concentrations: (b, b') 0 µM, (c) 20 µM, (d) 40 µM, (e) 60 µM, (f) 80 µM and (g) 100 µM. The response of glutathione solution solvent blank (c') 12 µL, (d') 24 µL, (e') 36 µL, (f') 48 µL and (g') 60 µL.
Figure 6B:
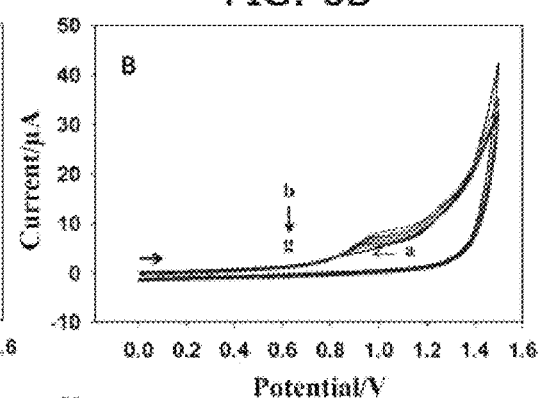
Figure 6C:
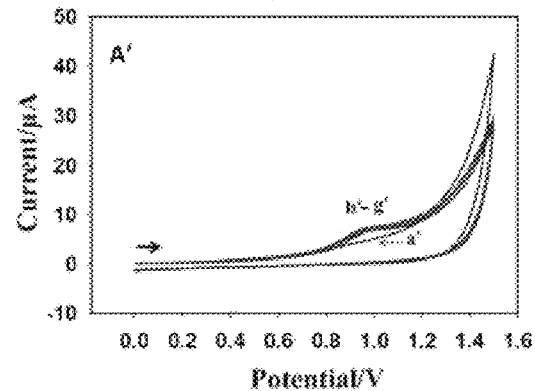
Figure 6D:
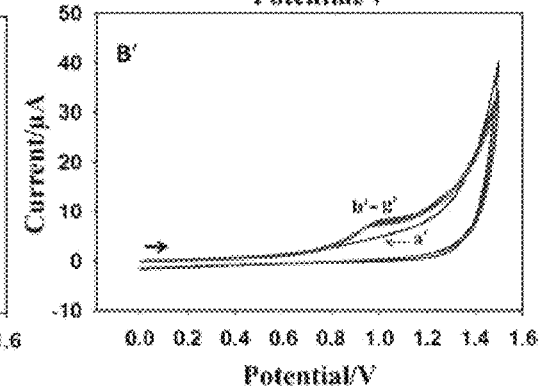

To get an insight into the reactivity of the complexes, the interactions of complexes 1 and 2 with model proteins, L-tyrosine, glutathione and lysozyme were studied electrochemically. The electrochemical behavior of complexes 1 and 2 in the presence of the proteins was analyzed by cyclic voltammetric technique (CV). As shown in FIG. 5, two CV irreversible anodic peaks appeared at +0.973 V and +0.982 V for complexes 1 and 2, respectively. The highly electroactive amino acid, L-tyrosine[49] was selected to demonstrate the degree of interaction of these anticancer compounds with amino acids. As a control experiment, the CV response of 0.1 mM complex 1, as shown in FIG. 5A(b), retained the same peak current intensity and peak shape even after spiking the same volume of the solvent blank used to prepare the L-tyrosine solution in the interaction study.

The sequential spiking of the L-tyrosine into a cell containing 0.1 mM complex 1 has shown a significant effect on the peak of the complex. At lower concentration levels of L-tyrosine, the peak of the complex decreased, and almost disappeared at around 320 μM of L-tyrosine (FIG. 5A(e)). A sharp peak of 320 μM L-tyrosine appeared at 0.654 V in absence of the gold compounds (FIGS. 5A(d) and 5B(d)). However, that peak was shifted to +0.712 V in the presence of complex 1 and its current significantly decreased (FIG. 5A(e)), which could be attributed to the interaction taking place between the drug and the L-tyrosine. Similar behavior was observed for complex 2 (FIG. 5B (d)) with a less peak shift observed +0.672 V compared to 1 (FIG. 5B(e)). Thus, the complex 1 is concluded to have more interaction with L-tyrosine.

The interaction of the compounds was also investigated with glutathione, which is a crucial antioxidant in animals. An interaction was observed for both complexes 1 and 2 with glutathione. The first spike of 20 μM of glutathione into 0.1 mM complex 1 or 2 caused a negative peak shift of the complexes to +0.942 and +0.955 V, respectively (FIG. 6). Subsequent spikes of glutathione into the electrochemical cell containing the 0.1 mM of 1 and 2 showed a systematic decrease in the registered peak currents of both complexes (FIGS. 6 A and B). In a control experiment (FIGS. 6 A' and B'), both compounds retained the same peak current.

Moreover, the interaction of these compounds was also explored with the Lysozyme protein attained from chicken egg white. The successive addition of Lysozyme into a solution containing 0.2 mM complexes 1 or 2 showed a decrease in the current intensities of the complex peaks. This interaction was more significant for the complex 1 compared to that of complex 2.

Example 2

In Vitro Cytotoxic Activity of Complexes

To examine the possible anticancer effect of complexes 1, 2, and cisplatin, a panel of three human tumor cell lines, A549 (lung cancer cells), MCF7 (breast cancer cells) and HCT15 (colon cancer cells) was used. The different human carcinoma cell cultures (A549, MCF7, HCT15) were first seeded at the concentration of $2 \times 10^4$ cells per mL in their respective growth mediums containing 10% FBS (fetal bovine serum) in a 96-well tissue culture plate and were incubated for 72 h at 37° C., 5% $CO_2$ in air and 90% relative humidity in a $CO_2$ incubator. After that the cell cultures were incubated for 24 h with 100 μL of cisplatin and the complexes (1-3) having 100, 50, 25 and 12.5 μM concentrations, prepared in growth medium. Further, the cultures were incubated with 100 μL of vital mitochondrial tetrazolium dye (3-(4,5-dimethylthiazol-2-yl)-2,5-diphenyltetrazolium bromide) (0.5 mg/ml) in a $CO_2$ incubator at 37° C. in the dark for 4 h. After incubation, purple colored formazan crystals were formed due to the reduction of dye by mitochondrial succinate dehydrogenase enzyme. The resultant crystals were solublized by adding 100 μL of dimethylsulfoxide (DMSO). The colored solution formed was thoroughly mixed and read spectrophotometrically at 570 nm with Lab systems Multiskan EX-Enzyme-linked immunosorbent assay (EX-ELISA) reader against a reagent blank. All data presented are mean±standard deviation.

The anticancer activity of complexes 1-3 as well as cisplatin was evaluated against a panel of representative human tumor cell lines, which include, lung cancer cells (A549), breast cancer cells (MCF7) and colon cancer cells (HCT15). The results of in vitro cytotoxic activity are expressed as $IC_{50}$ (concentration causing 50% reduction in cell viability) and are presented in Table 4. It can be seen that the investigated complexes displayed significantly greater cytotoxicity than cisplatin in all three cell lines (Table 4). Among the complexes, 3 exhibited the strongest antiproliferative potency, while 1 is the least active. For 1, the $IC_{50}$ values are closer to cisplatin. In going from 1 to 2, the substitution of two chlorine atoms by the chelating diamine ligand brought about a 1.5-3 times decrease in the antiproliferative activity of 2. The $IC_{50}$ values reported here are comparable to those obtained for the gold(III) complexes of 1,2-diaminocyclohexane (DACH) against SGC901 and PC3 cells reported in our previous studies.[19,22,23] While not being bound to any particular technical explanation or theory, complexes with bulky ligands and with greater degree of chelation may be more effective for the antiproliferative activity.

Figure 4A:
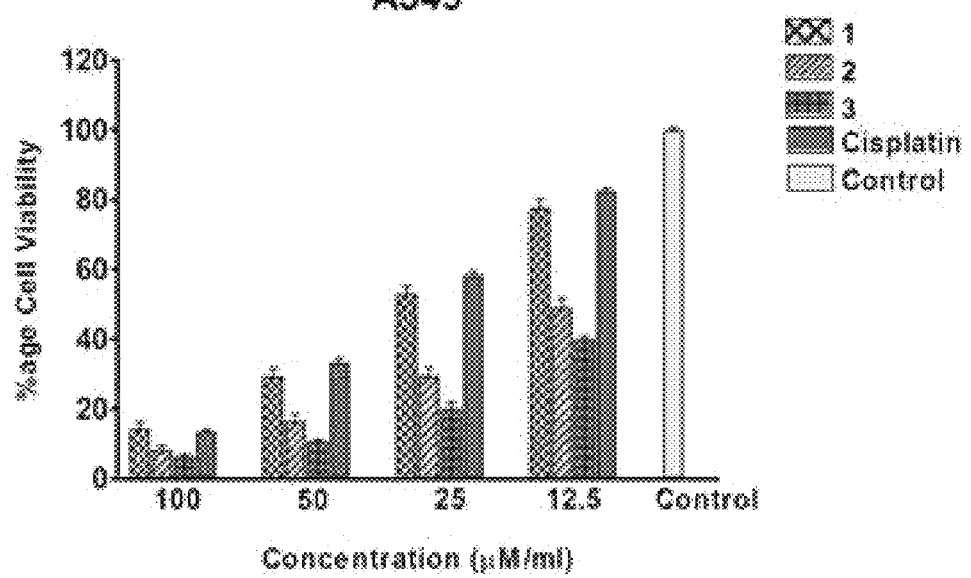
Figure 4B:
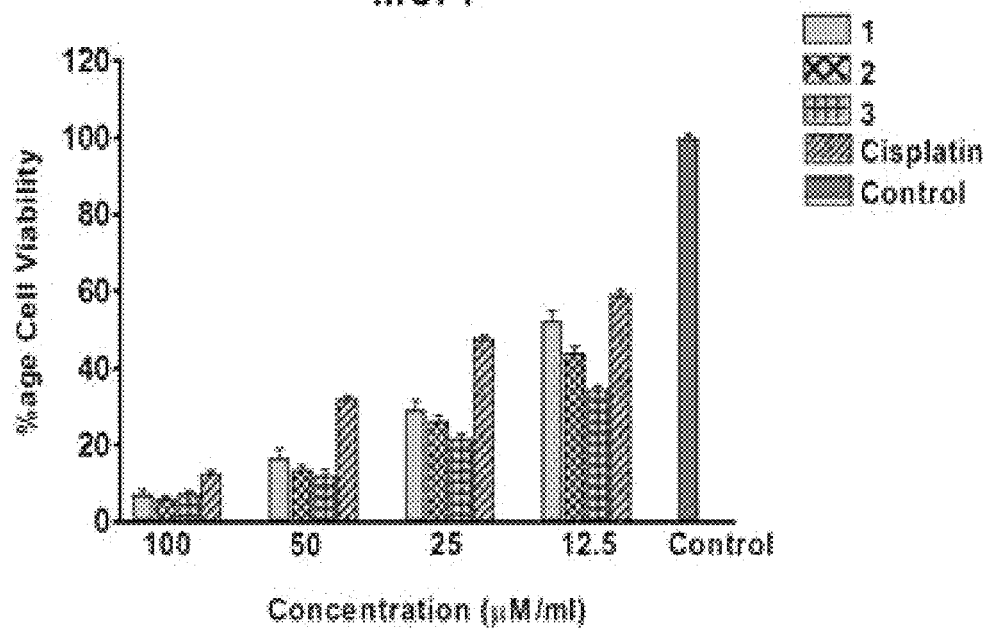

The survival of the cells (A549, MCF7 and HCT15) was studied by varying the concentration of complexes 1 and 2. The percentage of cell viability at various concentrations of gold(III) compounds is shown in FIGS. 4A, 4B and 4C. The data obtained represents the concentration-dependent cytotoxic effect against the human cancer cells. As the concentration decreases the cell viability increases. These data show that the gold(III) complexes of the invention are significantly better in reducing tumor cell viability than cisplatin.

TABLE 4

$IC_{50}$ Values (in µM) of Gold(III) complexes for different cell lines

| Complex | $IC_{50}$ | | |
|---|---|---|---|
| | A549 | MCF7 | HCT15 |
| 1 | 28.76 ± 4.02 | 11.85 ± 2.60 | 9.40 ± 1.93 |
| 2 | 10.34 ± 2.82 | 7.77 ± 1.82 | 4.23 ± 1.31 |
| Cisplatin | 42.88 ± 1.99 | 23.12 ± 3.78 | 23.12 ± 3.78 |

As shown by the Examples above, the inventors provide two new gold(III) complexes with a high degree of cytotoxic activity against different cancer cells. The structures of these gold(III) complexes have also been confirmed by analytical and spectroscopic data and the x-ray structure of compound 1 revealed that its gold atom adopts a square planar coordination environment. Both complexes 1 and 2 showed strong interaction with L-tyrosine, glutathione, and lysozyme protein and the gold(III) center remained stable during the reaction as indicated by cyclic voltammetric measurements. Complex 1 has a higher degree of interaction with L-tyrosine, glutathione and lysozyme protein than complex 2. However, both complexes 1 and 2 exhibited remarkable cytotoxic properties against several kinds of cancer cells.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the words "a" and "an" and the like carry the meaning of "one or more" unless the context clearly indicates otherwise.

Within the description of this disclosure, where a numerical limit or range is stated, the endpoints are included unless stated otherwise. Also, all values and subranges within a numerical limit or range are specifically included as if explicitly written out. For example, a range of 0 to 10 wt % includes 0. 0.25, 0.5, 1, 1.5, 2, 2.5, 3, 4, 5, 6, 7, 8, 9, 9.75, 9.99, <10, and 10.

The terms "including", "such as", "for example" and the like not tended to limit the scope of the present disclosure. They generally refer to one or more elements falling with a class or genus of other similar elements.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space into a link, for example, before "www" or after "//" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for inducing cytotoxicity against cancer cells in a subject in need thereof, comprising
administering a composition comprising a complex comprising Core (1) or a complex comprising Core (2), or both, one or more pharmaceutically acceptable excipients and a chemotherapeutic agent, into a site infiltrated by the cancer cells, while concurrently administering a radiation treatment to the subject;
wherein Core (1) and Core (2) have the following chemical structures:

Core (1)

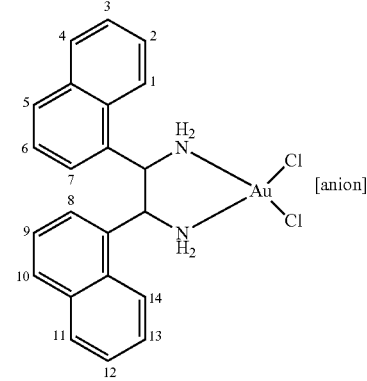

Core (2)

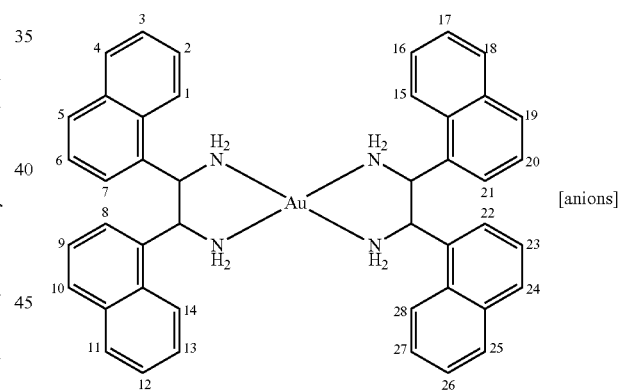

wherein positions 1-14 of Core (1) or positions 1-28 of Core (2) are, independently, hydrogen, hydroxy, halogen, C1-C6 alkyl, or aryl, and
wherein said anion is a halogen and said anions are three halogens;
wherein growth of said cancer cells is inhibited by said complex of Core (1) or Core (2),
wherein said cancer cells are selected from the group consisting of breast cancer cells, lung cancer cells and colon cancer cells.

2. The method of claim 1 that comprises administering [Au(npen)Cl$_2$]Cl.2H$_2$O ("complex 1"), wherein (npen) is meso-1,2-di(1-naphthyl)-1,2-diaminoethane.

3. The method of claim 1 that comprises administering [Au(npen)$_2$]Cl$_3$ ("complex 2"), wherein (npen) is meso-1,2-di(1-naphthyl)-1,2-diaminoethane.

* * * * *